(12) United States Patent
Quintaine et al.

(10) Patent No.: US 10,053,475 B2
(45) Date of Patent: Aug. 21, 2018

(54) HYDROGENATION OF ESTERS WITH FE/TRIDENTATE LIGANDS COMPLEXES

(71) Applicant: Firmenich SA, Geneva (CH)

(72) Inventors: Julie Quintaine, Geneva (CH); Lionel Saudan, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/105,927

(22) PCT Filed: Dec. 10, 2014

(86) PCT No.: PCT/EP2014/077217
§ 371 (c)(1),
(2) Date: Jun. 17, 2016

(87) PCT Pub. No.: WO2015/091158
PCT Pub. Date: Jun. 25, 2015

(65) Prior Publication Data
US 2016/0318956 A1    Nov. 3, 2016

(30) Foreign Application Priority Data
Dec. 18, 2013 (EP) ..................... 13198076

(51) Int. Cl.
| | | |
|---|---|---|
| *C07C 29/141* | (2006.01) | |
| *C07C 29/145* | (2006.01) | |
| *C07C 29/149* | (2006.01) | |
| *B01J 31/24* | (2006.01) | |
| *C07F 9/50* | (2006.01) | |
| *C07F 9/58* | (2006.01) | |
| *C07F 15/02* | (2006.01) | |

(52) U.S. Cl.
CPC ............ *C07F 9/5045* (2013.01); *B01J 31/24* (2013.01); *C07C 29/141* (2013.01); *C07C 29/145* (2013.01); *C07C 29/149* (2013.01); *C07F 9/5004* (2013.01); *C07F 9/5018* (2013.01); *C07F 9/5022* (2013.01); *C07F 9/582* (2013.01); *C07F 15/02* (2013.01); *B01J 2231/641* (2013.01); *B01J 2531/842* (2013.01)

(58) Field of Classification Search
CPC .... C07C 29/141; C07C 29/145; C07C 29/149
See application file for complete search history.

(56) References Cited

FOREIGN PATENT DOCUMENTS

| WO | WO2013171302 A1 | 11/2013 |
|---|---|---|
| WO | WO2013173930 A1 | 11/2013 |

OTHER PUBLICATIONS

International Search Report and Written Opinion, application PCT/EP2014/077217 dated Jan. 22, 2015.
Danapoulos, Edwards et al., Polyhedron, 1990, vol. 9, n° 19, 2413-2418.
Lagaditis, Morris et al., Inorg. Chem. 2010, 49, 3, 1094-1102.
Langer, Milstein et al., Angew. Chem. Int. Ed. 2011, 50, 9, 2120-2124.
Morris et al., J. Am. Chem. Soc. 2014, 136, 1367-1380.
Noyori et al., Angew.Chem.Int., 2001, 40, 40-73.
Saudan, Sustainable Catalysis, Wiley & Sons, 2013, 37-61C.

*Primary Examiner* — Medhanit W Bahta
(74) *Attorney, Agent, or Firm* — Winston & Strawn LLP

(57) ABSTRACT

The present invention relates to the field of catalytic hydrogenation and, more particularly, to the use of Fe complexes with tridentate ligands, having one amino or imino coordinating group and two phosphino coordinating groups, in hydrogenation processes for the reduction of ketones, aldehydes, esters or lactones into the corresponding alcohol or diol, respectively.

$$[Fe(L3)(L')Y_a](Z)_b \quad (1)$$

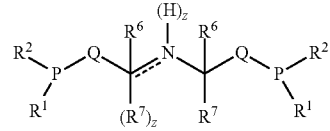

(A)

22 Claims, No Drawings

HYDROGENATION OF ESTERS WITH FE/TRIDENTATE LIGANDS COMPLEXES

This application is a 371 filing of International Patent Application PCT/EP2014/077217 filed 10 Dec. 2014, which claims the benefit of European patent application no 13198076.5 filed 18 Dec. 2013.

TECHNICAL FIELD

The present invention relates to the field of catalytic hydrogenation and, more particularly, to the use of Fe complexes with tridentate ligands, in hydrogenation processes for the reduction of esters, lactones, ketones or aldehydes into the corresponding alcohol or diol, respectively.

PRIOR ART

Reduction of an ester functional group to the corresponding alcohol is one of the fundamental reactions in organic chemistry, and is used in a large number of chemical processes. In general, two main types of processes are known to achieve such a transformation. Such types of processes are the following:
a) hydride processes, in which a silyl or metal hydride salt, such as $LiAlH_4$, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of an ester functional group represents still an important need in chemistry.

Amongst the few catalysts or catalytic systems known to perform such reductions one may cite the ruthenium/aminophosphine complexes, extensively reported in the literature (e.g. Noyori, R Angew. Chem. Int. Ed. 2001, 40, 40-73; Saudan, L. A. in Dunn, P. J.; Hii, K. K.; Krische, M. J.; Williams M. T. Editors. Sustainable Catalysis, J. Wiley & Sons, New Jersey; 2013, pp 37-61). However, such systems, although being highly performing suffer from requiring highly expensive and toxic ruthenium metal.

Very recently, Morris (see WO2013/173930) reported a first iron catalyst for the transfer hydrogenation of ketone, aldehydes or imine. The document is silent on esters, and is also silent on hydrogenations using $H_2$ as reducing agent, which is a reducing agent quite different from, and much more challenging of, a hydrogen donor.

Morris (see Inorg. Chem. 2010, 49, 1094) reported two imine compounds having acetonitrile as ligand, and wherein no activity or use is reported or suggested.

Milstein (see Angew. Chem. Int. Ed, 2011, 50, 2120) reported an aldehyde, ketone hydrogenation using an iron complex with a tridentate pyridine derivative. The document is silent on esters reductions and shows weak selectivity on enones/enals as well as moderate activity toward standard aldehyde, ketone.

Therefore, there is a need for hydrogenation processes using alternative catalysts or pre-catalysts, preferably having a greater diversity in the ligand structures and coordination spheres around the metal center and presenting a broader spectrum of substrates and if possible with enhanced selectivity.

DESCRIPTION OF THE INVENTION

In order to overcome the problems aforementioned, the present invention relates to processes for the reduction by hydrogenation, using molecular $H_2$, of a $C_3$-$C_{70}$ substrate containing one or two carbonyl or carboxylic functional group (e.g selected amongst ester, lactone, ketone or aldehyde) into the corresponding alcohol, or diol, characterized in that said process is carried out in the presence of a base and at least one catalyst or pre-catalyst in the form of a iron complex of a tridentate ligand wherein the coordinating groups consist of one amino or imino group and two phosphino group.

According to an embodiment of the invention, said amino group is a primary (i.e. $NH_2$) or a secondary (i.e. NH) amino group.

According to a particular embodiment of the invention, the substrate can be a compound of formula (I)

wherein n represents 0 or 1;
$R^a$ and $R^b$, taken together, represent a $C_3$-$C_{20}$, preferably $C_4$-$C_{20}$, hydrocarbon group, optionally substituted and optionally comprising one, two or three oxygen or nitrogen atoms; or, when said $R^a$ and $R^b$ are taken separately,
$R^a$ represents a hydrogen atom or a $R^b$ group; and
$R^b$ represents a $C_1$-$C_{30}$ hydrocarbon group, optionally substituted and optionally comprising one, two or three oxygen or nitrogen atoms.

When n is 1, the corresponding alcohols (i.e (II-a) and (II-b)), or the corresponding diol (II'), of said substrate (I), are of formula

wherein $R^a$ and $R^b$ are defined as in formula (I). In such a case, a compound of formula (II-a) or (II-b) will be obtained in the case where $R^a$ and $R^b$ are not bonded together, while a compound of formula (II') will be obtained in the case where $R^a$ and $R^b$ are bonded together.

When n is 0, the corresponding alcohol (i.e (II-c) and (II-b)), is of formula

(II-c)

wherein $R^a$ and $R^b$ are defined as in formula (I).

It is understood that by " . . . hydrocarbon group . . . " it is meant that said group can be in the form of a linear, branched or cyclic aromatic, alkyl, alkenyl, alkandienyl or alkynyl group, e.g., a cyclic alkyl group, or can also be in the form of a mixture of said type of groups, e.g. a specific group may comprise a linear alkyl, a branched alkandienyl (e.g. having one or more carbon-carbon double bonds), a (poly) cyclic alkyl and an aryl moiety, unless a specific limitation to only one type is mentioned. Similarly, in all the below embodiments of the invention, when a group is mentioned as being in the form of more than one type of topology (e.g. linear, cyclic or branched) and/or unsaturation (e.g. alkyl, aromatic or alkenyl), it is meant also a group which may comprise moieties having any one of said topologies or unsaturations, as explained above. Similarly, in all the below embodiments of the invention, when a group is mentioned as being in the form of one type of unsaturation, (e.g. alkyl), it is meant that said group can be in any type of topology (e.g. linear, cyclic or branched) or having several moieties with various topologies.

In a particular embodiment of the invention's process, the substrate is an ester or lactone of formula

(I-a)

wherein $R^a$ and $R^b$ are defined as in formula (I).

In a particular embodiment of the invention's process, the substrate is an aldehyde or ketone of formula

(I-b)

wherein $R^a$ and $R^b$ are defined as in formula (I).

According to any one of the embodiments of the invention, said aldehyde, ketone ester or lactone, is one that will provide an alcohol, or a diol, that is useful in the pharmaceutical, agrochemical or perfumery industry as final product or as an intermediate. Particularly preferred substrate is an aldehyde, ketone, ester or lactone, which will provide an alcohol, or diol, which is useful in the perfumery industry as final product or as an intermediate.

According to any one of the embodiments of the invention, the substrate is a $C_5$-$C_{30}$ compound of formula (I), or even a $C_5$-$C_{20}$ compound of formula (I).

According to any one of the embodiments of the invention, one may cite as substrate the one wherein $R^a$ represents a hydrogen atom or a $R^b$ group, and each $R^b$, when taken separately, represents simultaneously or independently a linear, branched or cyclic $C_1$-$C_{30}$ aromatic, alkyl, alkenyl or alkanedienyl group optionally substituted and optionally comprising one or two oxygen or nitrogen atoms; or $R^a$ and $R^b$ are bonded together and form a $C_4$-$C_{20}$ saturated or unsaturated linear, branched, mono-, di- or tri-cyclic group, optionally substituted and optionally comprising one or two oxygen or nitrogen atoms.

According to any one of the embodiments of the invention, one may cite as substrate those wherein $R^a$ represent a hydrogen atom or a $R^b$ group, and each $R^b$, when taken separately, represent simultaneously or independently a linear, branched or cyclic $C_3$-$C_{18}$ aromatic, alkyl, alkenyl or alkanedienyl group optionally substituted; or $R^a$ and $R^b$ are bonded together and form a $C_5$-$C_{20}$ saturated or unsaturated linear, branched, mono-, di- or tri-cyclic group, optionally substituted.

According to any one of the embodiments of the invention, when n is 1 and $R^a$ is an alkenyl or alkadienyl group, that said group is not an alk-1-enyl or an alka-1,3-dienyl group (i.e. the carbon carbon double bonds are not conjugated with the ester group).

According to any one of the above embodiments of the invention, when n is 0 and $R^a$ is an alkenyl or alkadienyl group, that said group is an alk-1-enyl or an alka-1,3-dienyl group (i.e. the carbon carbon double bonds are conjugated with the ester group).

According to any one of the above embodiments of the invention, when n is 0 and $R^a$ is a hydrogen atom, $R^b$ may represent in particular a branched or cyclic hydrocarbon group wherein the branching is in the alpha position relative to the CHO group of the substrate.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

According to a particular aspect of the invention, the possible substituents of $R^a$ and $R^b$ are one or two halogen, $OR^c$, $NR^c_2$ or $R^c$ groups, in which $R^c$ is a hydrogen atom, a $C_1$ to $C_6$ cyclic, linear or branched alkyl, or alkenyl group, preferably a $C_1$ to $C_4$ linear or branched alkyl or alkenyl group.

Non-limiting examples of substrates of formula (I) are the following:

$C_{3-14}$ aldehydes such as:
a $C_{3-10}$ alkanal, a $C_{3-10}$ 2-alkenal, a $C_{3-10}$ 2-methyl-2-alkenal, a $C_{5-10}$ 2,4-dienal, a 3-alkyl-3-benzene-prop-2-enal, a 3-alkyl-2-methyl-3-benzene-prop-2-enal, a $C_{7-10}$-benzene-carbaldehyde, a $C_{4-12}$ 2-methylen-aldehyde;
wherein the underlined compounds are known to be particularly base-sensitive substrates;

$C_{3-17}$ ketones such as:
a di($C_{1-12}$ alkyl) ketone, a $C_4$-$C_{12}$ cyclic-ketone, a cyclopentenone alpha substituted by a $C_{5-12}$ hydrocarbon group, a cyclohexenone alpha substituted by a $C_{6-12}$ hydrocarbon group, a substituted aryl $C_{1-12}$-alkyl ketone, a $C_{2-12}$-1-alkene methyl ketone, a $C_{2-15}$-2-alkene-1,1-dimethyl methyl ketone, a $C_{2-15}$-2-alkyl-1,1-dimethyl methyl ketone; and $C_{6-14}$ esters such as:

alkyl cinnamates, alkyl or glycolic esters of natural (fatty or not) acids, Sclareolide, spirolactones, allylic ester, di alkyl diesters, (un)substituted benzoic esters, β-γ and/or ω-unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid and 10-undecenoic acid alkyl esters and 9-decenoic acid alkyl esters. One can also cite the di alkyl esters of 1,4-dicarboxylate-cyclohexane, the di $C_{1-5}$ alkyl esters of the $C_{2-10}$ alkanediyl-dicarboxylates, $C_{1-5}$ alkyl cyclopropanecarboxylates, mono-, di- or tri-methoxybenzoic esters.

The process of the invention is characterized by the use, as catalyst or pre-catalyst (hereinafter referred to as complexes unless specified otherwise), of an iron complex as described above. The complex can be in the form of an ionic or neutral species.

According to an embodiment of the invention, the iron complex can be of the general formula

[Fe(L3)(L')$Y_a$](Z)$_b$  (1)

wherein L3 represents a tridentate ligand wherein the coordinating groups consist of one amino or imino group and two phosphino groups;

L' represents a CO or $C_{1-11}$ isonitrile compound;

each Y represents, simultaneously or independently, a hydrogen or halogen atom, a hydroxyl group, or a $C_1$-$C_6$ alkoxy or carboxylic radical or a $BH_4$ or $AlH_4$ group;

each Z represents, simultaneously or independently, a halogen atom, a hydroxyl group, or a $C_1$-$C_6$ alkoxy or carboxylic radical or a $BH_4$ or $AlH_4$ group; and (a+b)=2 with a being 1 or 2.

In a particular embodiment of the invention, said L3 ligand may be a $C_6$-$C_{40}$, or even a $C_6$-$C_{30}$, compound.

According to any embodiment of the invention, in formula (1), each Y represents, simultaneously or independently, a hydrogen or chlorine or bromine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical or a $BH_4$ group. More preferably, each Y represents, simultaneously or independently, a hydrogen or chlorine or bromine atom, a methoxy, ethoxy or isopropoxy radical, or a $BH_4$ group.

According to any embodiment of the invention, in formula (1), each Z represents, simultaneously or independently, a chlorine or bromine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical or a $BH_4$ group. More preferably, each Z represents, simultaneously or independently, a chlorine or bromine atom, a methoxy, ethoxy or isopropoxy radical, or a BH4 group.

According to any embodiment of the invention, L' represents a CO.

According to any embodiment of the invention, there can be used as complex a compound of one of the formula

[Fe(L3)(L')$Y_2$]  (2)

wherein L3 L' and Y have the meaning indicated above.

According to any one of the above-mentioned embodiments, the tridentate ligand L3 can be a compound of one of the formula

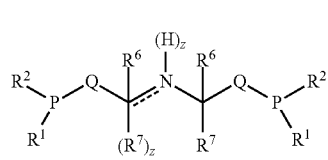

wherein the dotted line indicates a single or double bond;

z is 0 or 1 when the carbon-nitrogen bond with the dotted line represents a double or single bond respectively;

$R^1$ and $R^2$, when taken separately, represent, simultaneously or independently, a linear, branched or cyclic $C_1$ to $C_{10}$ alkyl or alkenyl group optionally substituted, a $C_6$ to $C_{10}$ aromatic group optionally substituted; said groups $R^1$ and $R^2$, when taken together, may form a saturated or unsaturated ring optionally substituted, having 5 to 10 atoms and including the phosphorus atom to which said $R^1$ and $R^2$ groups are bonded;

$R^6$ and $R^7$ represent, simultaneously or independently, a hydrogen atom, a linear, branched or cyclic $C_1$ to $C_6$ alkyl or alkenyl group optionally substituted, a $C_6$-$C_{10}$ aromatic group optionally substituted; when the dotted line represent a single bond, two $R^6$ taken together, may form a saturated heterocycle, optionally substituted and optionally containing one or two additional nitrogen or oxygen atoms, containing 5 to 10 atoms and including the N atom and the carbon atoms to which said $R^6$ groups are bonded respectively; and Q represents:

a group of formula

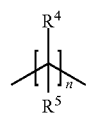

wherein n is an integer from 1 to 3, and $R^4$ and $R^5$ represent, simultaneously or independently, a hydrogen atom, a linear, branched or cyclic $C_1$ to $C_6$ alkyl or alkenyl group optionally substituted, a $C_6$-$C_{10}$ aromatic group optionally substituted; two distinct $R^4$ and/or $R^5$ groups, taken together, may form a $C_5$ to $C_8$, saturated ring optionally substituted, including the carbon atoms to which each of said $R^4$ or $R^5$ group is bonded; or a diphenyl, dinaphthyl, $C_5$-$C_{12}$ metallocediyl, phenylene or naphthylene group optionally substituted.

According to any embodiment of the invention, by "aromatic group or ring" it is meant a phenyl or naphthyl derivative.

For the sake of clarity, by the expression "wherein one dotted line represents a single or double bond", or the similar, it is meant the normal meaning understood by a person skilled in the art, i.e. that the whole bonding (solid and dotted line) between the carbon and nitrogen atoms connected by said dotted line, is a carbon-nitrogen single or double bond.

According to any one of the above-mentioned embodiments, the tridentate ligand L3 can be a compound of one of the formula

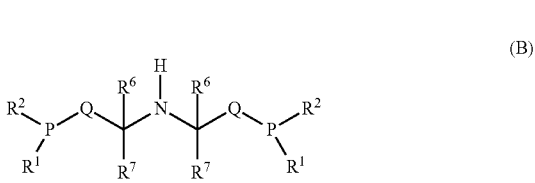

(B)

wherein the $R^1$, $R^2$, $R^6$ and $R^7$ have the meaning indicates in formula (A).

According to any embodiment of the invention, $R^1$ and $R^2$, when taken separately, represent, simultaneously or independently, a linear, branched or cyclic $C_1$ to $C_{10}$ alkyl group optionally substituted, a $C_6$-$C_{10}$ phenyl or naphthyl group optionally substituted; said groups $R^1$ and $R^2$, when taken together, may form a saturated ring optionally substituted, having 5 to 10 atoms and including the phosphorus atom to which said $R^1$ and $R^2$ groups are bonded.

According to any embodiment of the invention, $R^1$ and $R^2$ are taken separately and each represent, simultaneously or independently, a linear, branched or cyclic $C_1$, or even $C_3$, to $C_6$ alkyl group optionally substituted, a phenyl group optionally substituted.

According to any embodiment of the invention, $R^6$ and $R^7$ represent, simultaneously or independently, a hydrogen atom, a linear, branched or cyclic $C_1$ to $C_6$ alkyl group optionally substituted, a phenyl group optionally substituted; when the dotted line represent a single bond, two $R^6$ taken together, may form a saturated heterocycle, optionally substituted and optionally containing one additional nitrogen or oxygen atoms, containing 5 or 6 atoms and including the N atom and the carbon atoms to which said $R^6$ groups are bonded respectively.

According to any embodiment of the invention, one or two $R^7$ are hydrogen atoms. Similarly one or two $R^6$ are hydrogen atoms.

According to any embodiment of the invention, Q represents:

a group of formula

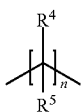

(i)

wherein n is 1 or 2, and $R^4$ and $R^5$ represent, simultaneously or independently, a hydrogen atom, a linear, branched or cyclic $C_1$ to $C_6$ alkyl group optionally substituted, a $C_6$-$C_{10}$ phenyl or naphthyl group optionally substituted; or a $C_5$-$C_{12}$ ferrocenediyl, 1,2-phenylene or 1,2- or 2,3-naphthylene group optionally substituted.

According to any embodiment of the invention, Q represents a group of formula (i) wherein n is 1 or 2, and $R^4$ and $R^5$ represent, simultaneously or independently, a hydrogen atom, a linear, branched or cyclic $C_1$ to $C_6$ alkyl group optionally substituted, a phenyl group optionally substituted.

According to any embodiment of the invention, Q represents a linear methylene or ethylene group optionally substituted.

According to any embodiment of the invention, possible substituents of $R^4$, $R^5$, $R^6$ and $R^7$ are one or two halogen, $C_1$ to $C_{10}$ alkoxy groups, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

According to any embodiment of the invention, possible substituents of $R^4$, $R^5$, $R^6$ and $R^7$ are one or two halogen, $C_1$ to $C_6$ alkoxy groups, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups.

Possible substituents of $R^1$ and $R^3$ and Q, in particular when said groups are or contain phenyl or aromatic groups or moieties, one to three $C_1$ to $C_5$ alkoxy groups, $C_1$ to $C_4$ alkyl groups, or NR groups, wherein R is a $C_1$ to $C_6$ alkyl $C_5$ to $C_6$ cycloalkyl.

The processes of the invention are particularly attractive when are used complexes of the (2) $[Fe(L3)(CO)Y_2]$ wherein Y has the meaning indicated above and L3 represents a ligand of the formula (C):

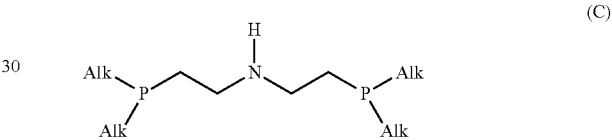

(C)

wherein Alk is a $C_{3-10}$, or even $C_{3-6}$, branched or cyclic alkyl group.

The complexes according to the invention are also new, and are therefore also another object of the present invention.

The ligands described above can be obtained by applying standard general methods which are well known in the state of the art and by the person skilled in the art.

Therefore, their preparation does not require a specific description. For example one may revert to Edwards, P. G. *Polyhedron* 1990, 9, 2413-2418.

In a general way, the complexes of formula (1) or (2) can be prepared and isolated prior to their use in the process according to the general methods described in the literature. A method is described in the Example.

Moreover, the complexes can be prepared in situ, by several methods, without isolation or purification, just before their use as described in the Example or also one may use as starting complexes the ones of formula $$[Fe(L3)(L'')_3Y_a](Z)_b \qquad (3)$$

wherein L3, Y, Z, a and b are as defined above; and

L'' represents a $C_{1-11}$ nitrile compound;

which are then either reacted with a isonitrile or contacted with a CO containing atmosphere, such as a mixture of $H_2$ and CO.

To carry out the processes of the invention, it is required also to use a base. Said base can be the substrate itself, if the latter is basic, a corresponding alcoholate or any base having preferentially a $pK_a$ above 10, or even above 11. According to a particular embodiment of the invention said base may have a $pK_a$ above 14. It is also understood that preferably said base does not reduce itself a substrate of formula (I). As non-limiting examples one may cite the following type of base: alcoholate, hydroxides, alkaline or alkaline-earth carbonates, phosphazenes, amides, basic alox, siliconates (i.e. silicium derivatives having SiO⁻ or SiRO⁻ groups), hydrides such as $NaBH_4$, NaH or KH.

One can cite, as non-limiting examples, alkaline or alkaline-earth metal carbonates, such as cesium carbonate, an alkaline or alkaline-earth metal hydroxides, $C_{1-10}$ amidures, $C_{10-26}$ phosphazene or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical, such as sodium or potassium alcoholates. Of course, other suitable bases can be used.

According to an embodiment of the invention, said base is an alkaline alcoholate of formula $R^{13}OM'$.

As previously mentioned the processes of the invention consist in the hydrogenation of a substrate using an iron complex and a base. A typical process implies the mixture of the substrate with the iron complex, a base and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 50 ppm to 50000 ppm, relative to the amount of substrate. Preferably, the complex concentration will be comprised between 100 and 20000 ppm, or even between 500 and 10000 ppm. It goes without saying that the optimum concentration of complex will depend, as the person skilled in the art knows, on the nature of the latter, on the nature of the substrate and on the pressure of $H_2$ used during the process, as well as the desired time of reaction.

Useful quantities of base, added to the reaction mixture, may be comprised in a relatively large range. One can cite, as non-limiting examples, ranges between 0.0005 to 0.2 molar equivalents, relative to the substrate, preferably 0.001 to 0.10, and even more preferably between 0.01 to 0.05 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene or xylene, hydrocarbon solvents such as hexane or cyclohexane, ethers such as tetrahydrofuran or MTBE, polar solvents such as primary or secondary alcohols such as isopropanol or ethanol, or mixtures thereof. The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bar) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bar).

According to a particular embodiment of the invention, the atmosphere of the reaction medium may also contain about 0.001 and 0.10%, or even 0.01 and 0.05%, of CO relative to the molar amount of $H_2$.

The temperature at which the hydrogenation can be carried out is comprised between 0° C. and 120° C., more preferably in the range of between 20° C. and 100° C., or even between 30° C. and 80° C. Of course, a person skilled in the art is also able to select the preferred temperature as a function of the melting and boiling point of the starting and final products as well as the desired time of reaction or conversion.

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out either in open glass tubes placed inside a stainless steel autoclave or directly in the autoclave. $H_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CD_2Cl_2$ unless indicated otherwise. Chemical shifts are listed in ppm downfield from tetramethylsilane. $^{31}$P NMR chemical shifts are reported in ppm downfield from $H_3PO_4$ and referenced to an external 85% solution of phosphoric acid in $D_2O$ as standard.

EXAMPLES

Example 1

Preparation of Carbonyl dibromo bis[2-(di-isopropylphosphino)ethyl] amine iron (II) (Fe(L-1)(CO)Br₂)

Under argon to a stirred solution of $FeBr_2$ (394.6 mg, 1.83 mmol) in THF (15 ml) in a heavy wall glass tube, was added a solution of ligand L-1 (561.8 mg, 1.84 mmol) in THF (2 ml). More THF (3×1 ml) was added to rinse. A white solid precipitated immediately and more THF (5 ml) was added to facilitate the stirring which was continued for another 1 hour. The vessel was pressurised under a CO atmosphere (2 bar) leading after a few minutes to a clear deep blue solution. After 2 h, the CO atmosphere was depressurised to give a deep blue solution which was stirred under argon overnight (17 h) before concentration under vacuum to give a blue solid. The solid was dissolved in $CH_2Cl_2$ (4 ml), the solution was filtered and added to hexane (30 ml) to give the desired complex as a blue solid which was recovered by filtration and dried under vacuum (823.2 mg, 1.44 mmol, 79%).

$^1$H-NMR: 1.36-1.48 (m, 24H), 2.09 (m, 2H), 2.51 (m, 2H), 2.77 (m, 4H), 3.45 (brq, 2H, J=12.7 Hz), 3.71 (m, 2H), 5.4 (brt, 1H).

$^{13}$C-NMR: 19.31 (d, 2C, JCP=30.4 Hz, PCH(CH₃)₂), 20.1 (d, 2C, JCP=45.7 Hz, PCH(CH₃)₂), 23.8 (t, 1C, JCP=9.55 Hz), 25.5 (t, 1C, JCP=11.0 Hz), 26.9 (t, 1C, JCP=7.1 Hz), 50.9 (t, 1C, JCP=4.55 Hz, NHCH₂), 227.8 (t, 1C, JCP=22.9 Hz, Fe—CO).

$^{31}$P{$^1$H}-NMR: 67.9 (s).

Example 2

Preparation of Carbonyl hydridobromo bis[2-(di-isopropylphosphino)ethyl] amine iron (II) (Fe(L-1)(CO)HBr)

Under argon to a cold (−20° C.) and stirred solution of Fe(L-1)(CO)Br₂ (55.3 mg, 0.1 mmol) in THF (2 ml) was added a solution of NaEt₃BH (0.1 ml at 1M in THF, 0.1 mmol). The resulting yellow brown suspension was stirred at RT for 1 h and then let standing at RT for 19 h. Then THF (2 ml) was added and the suspension was filtered (Acrodisc PTFE 1 micron) and the filtrate was concentrated under vacuum to give an orange brown solid. The solid was washed with cold (−20° C.) hexane (2 ml) and dried under vacuum (0.1 mbar) to give a yellow orange solid (35.1 mg, 0.075 mmol, 74%).

$^1$H-NMR: −22.7 (t, 1H, JHP=52.9 Hz, Fe—H), 0.87 (brs, 6H), 1.17 (brm, 12H), 1.66 (brm, 12H), 2.04 (brs, 2H), 2.48 (brs, 2H), 3.1 (brs, 2H), 3.4 (brs, 1H).

$^{31}$P{$^1$H}-NMR: Presence of two isomers along with some dihydride: 93.3 (d, JPH=Hz, 90%), 94.9 (d, JPH=Hz, 8%), 109.4 (s, 2%).

Example 3

Catalytic Hydrogenation of Aldehydes and Ketones Using Complexes Fe(L-1)(CO)HBr A typical experimental procedure is as follows:

A Keim autoclave was charged successively with Fe(L-1)(CO)HBr (4.8 mg, 0.01 mmol, 0.1 mol %), a solution of acetophenone (1.2053 g, 10 mmol) in EtOH (1 ml), more EtOH (3×1 ml) was added to rinse followed by a solution of KO$^t$Bu (2.4 mg, 0.021 mmol, 0.2 mol %) in EtOH (2 ml) and more EtOH (2×1 ml) was added to rinse. The autoclave was pressurised with hydrogen gas at 20 bars and the solution was stirred at RT. After 18 hour, the autoclave was depressurized, GC (DB-Wax) analysis showed a full conversion. The solvent was removed in vacuo to give a yellow liquid which was purified by Kugelrohr distillation (bp 60-110° C./13-5 mbar) giving pure 1-phenylethanol (1.158 g, 9.48 mmol, 95%) as a colourless liquid.

$^1$H NMR (CDCl$_3$): 1.46 (d, J=6.5 Hz, 3H), 2.16 (s, 1H), 4.84 (q, J=6.5 Hz, 1H), 7.23-7.27 (m, 1H), 7.30-7.35 (m, 4H).

$^{13}$C NMR (CDCl$_3$): 25.12 (CH3), 70.33 (CH), 125.39 (CH), 127.42 (CH), 128.46 (CH), 145.84 (C).

Under these conditions, several aldehydes and ketones as reported in Table 1 were tested. The results are reported in Table 2.

TABLE 1

Structure and names of aldehydes and ketones used

| Substrate | Structure | Name |
|---|---|---|
| 1 | 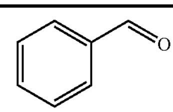 | Benzaldehyde |
| 2 | 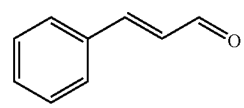 | Cinnamaldehyde |
| 3 | 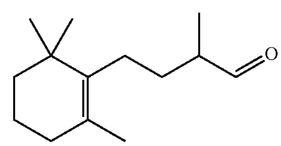 | 2-Methyl-4-(2,6,6-trimethylcyclohex-1-en-1-yl)butanal |
| 4 | 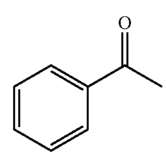 | Acetophenone |
| 5 | 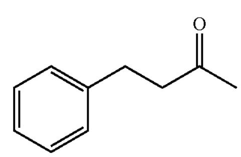 | 4-Phenylbutan-2-one |
| 6 | 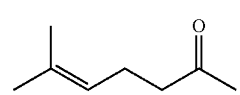 | 6-Methylhept-5-en-2-one |
| 7 | 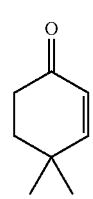 | 4,4-Dimethylcyclohex-2-enone |

TABLE 1-continued

Structure and names of aldehydes and ketones used

| Substrate | Structure | Name |
|---|---|---|
| 8 | 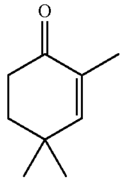 | 2,4,4-Trimethylcyclohex-2-enone |
| 9 | 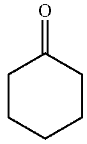 | Cyclohexanone |
| 19 | 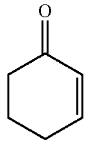 | Cyclohex-2-enone |
| 20 | 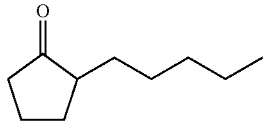 | 2-Pentylcyclopentanone |
| 21 | 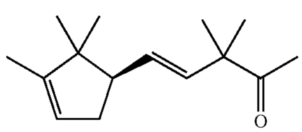 [SMILES: CC(=O)C(C)(C)/C=C/[C@H]1CC=C(C)C1(C)C] | (R,E)-3,3-Dimethyl-5-(2,2,3-trimethylcyclopent-3-en-1-yl)pent-4-en-2-one |
| 22 | 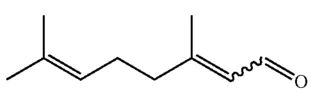 | 3,7-Dimethylocta-2,6-dienal |

TABLE 2

Hydrogenation of ketones using complex Fe(L-1)(CO)HBr

| Test | Sub. | C/B | Conv. | Isolated yield |
|---|---|---|---|---|
| 1 | 4 | 1000/2000 | >99 | 94 |
| 2 | 5 | 1000/2000 | 80 | — |
| 3 | 5[1] | 1000/2000 | >99 | 96 |
| 4 | 19[2] | 1000/10000 | >99 | 90[3] |
| 5 | 20[4] | 1000/10000 | >99 | 100[5] |
| 6 | 21[6] | 5000/50000 | >99 | 96[7] |
| 7 | 22[4] | 1000/10000 | 97 | 90[8] |

C/B: catalyst/base ratio in ppm relative to the substrate.
Conv.: Conversion (in %, analysed by GC) of ketones to the corresponding alcohol after 18 hour.
Reaction conditions: $H_2$ gas (20 bar), 25° C., EtOH (1.7M).
[1]Test performed at 50° C. during 9 h 30 min.
[2]Test performed in THF (1.7M) at 50° C. under $H_2$ gas (25 bar) for 16 h.
[3]Amount observed by GC (DB-Wax) as well as some cyclohexanol (10%).
[4]Test performed in EtOH (1.7M) at 50° C. under $H_2$ gas (25 bar) for 16 h.
[5]Amount observed by GC (DB-Wax) as a mixture of cis (99%) and trans (1%) isomers.
[6]Test performed in THF (1.7M) at 100° C. under $H_2$ gas (50 bar) for 16 h with NaOMe (5 mol %).
[7]Mixture of two isomers (66/34).
[8]Amount observed by GC (DB-Wax).

Example 4

Catalytic Hydrogenation of Aldehydes and Ketones Using Complexes Fe(L-1)(CO)Br$_2$ A typical experimental procedure is as follows:

In a Keim autoclave, charged with a solution of benzaldehyde (1.0764 g, 10 mmol) in EtOH (5 ml) was added with a syringe a solution of Fe(L-1)(CO)HBr (0.5 ml at 0.02M in THF, 0.01 mmol, 0.1 mol %), prepared by adding at −20° C. a solution of NaEt$_3$BH (0.035 ml at 1M, 0.035 mmol) to a solution of Fe(L-1)(CO)Br$_2$ (16 mg, 0.03 mmol) in THF (1.5 ml) and stirring for 30 min at RT, followed by solid KO$^t$Bu (11.0 mg, 0.1 mmol, 1 mol %). The autoclave was pressurised with hydrogen gas at 20 bars and placed in a heating block set at 50° C. After 16 hour, the autoclave was removed and cooled to RT. The solvent was removed in vacuo to give a yellow liquid which was purified by Kugelrohr distillation (80° C./0.4 mbar) to give benzyl alcohol (0.962 g, 8.54 mmol, 84%) as a colourless liquid (GC purity 96%).

$^1$H NMR (CDCl$_3$): 7.38-7.25 (m, 5H), 4.65 (s, 2H), 2.02 (s, 1H).

$^{13}$C NMR (CDCl$_3$): 140.9 (s), 128.6 (d), 127.6 (d), 126.9 (d), 62.3 (t).

Under these conditions, several aldehydes and ketones as reported in Table 1 were tested. The results are reported in Table 3.

TABLE 3

Hydrogenation of aldehydes and ketones using complex Fe(L-1)(CO)Br$_2$

| Test | Sub. | C/B | Conv. | ROH | Sel. | Isolated yield |
|---|---|---|---|---|---|---|
| 1 | 1 | 1000/10000 | >99 | 96 | — | 84 |
| 2 | 2 | 1000/10000 | 99 | 95 | >99 | 74 |
| 3 | 3 | 1000/10000 | >99 | 94 | >99 | 93 |
| 4 | 6 | 1000/10000 | >99 | >99 | >99 | 85 |
| 5 | 7 | 1000/10000 | >99 | 93 | >99 | 76 |
| 6 | 8 | 1000/10000 | >99 | >99 | >99 | 76 |
| 7 | 9[a] | 1000/10000 | >99 | >99 | — | — |

C/B: catalyst/base ratio in ppm relative to the substrate.
Conv.: Conversion (in %, analysed by GC) of aldehydes or ketones to the corresponding alcohol after 16 hours. Reaction conditions: H$_2$ gas (20 bar), 50° C., EtOH (2M).
ROH: amount of alcohol in percent in the reaction mixture as analysed by GC
Sel.: Selectivity given as ratio between unsaturated and saturated alcohol as analysed by GC.
[a]Test performed at room temperature during 6 hours.

Example 5

Catalytic Hydrogenation of Esters Using Complexes Fe(L-1)(CO)Br$_7$

A typical experimental procedure is as follows:

In a Keim autoclave, charged with a solution of methylbenzoate (1.3599 g, 10 mmol) in THF (5 ml) was added with a syringe a solution of Fe(L-1)(CO)HBr (1 ml at 0.02M in THF, 0.02 mmol, 0.2 mol %), prepared by adding at −20° C. a solution of NaEt$_3$BH (0.1 ml at 1M, 0.1 mmol) to a solution of Fe(L-1)(CO)Br$_2$ (45 mg, 0.08 mmol) in THF (4 ml) and stirring for 30 min at RT, followed by solid NaOMe (0.027 g, 0.5 mmol, 5 mol %). The autoclave was pressurised with hydrogen gas at 50 bars and placed in a heating block set at 100° C. After 16 hour, the autoclave was removed and cooled to RT. The reaction mixture was diluted with MTBE (5 ml) and washed with a solution of sat. aq. NH$_4$Cl (5 ml). The organic layer was dried over anh. Na$_2$SO$_4$ and filtered. Then the solvent was removed in vacuo to give a yellow liquid which was purified by Kugelrohr distillation (80° C./0.4 mbar) to give pure benzyl alcohol (0.968 g, 8.86 mmol, 89%) as a colourless liquid.

Under these conditions, several esters as reported in Table 4 were tested. The results are reported in Table 5.

TABLE 4

Structure and names of esters used

| Substrate | Structure | Name |
|---|---|---|
| 10 | 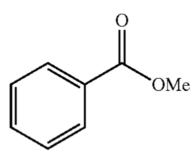 | Methyl benzoate |
| 11 | 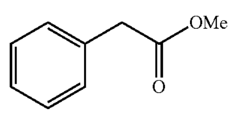 [SMILES: COC(=O)Cc1ccccc1] | Methyl 2-phenylacetate |
| 12 | 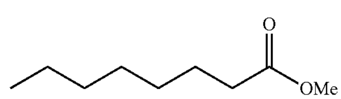 | Methyl octanoate |
| 16 | 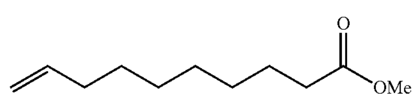 | Methyl dec-9-enoate |
| 17 | 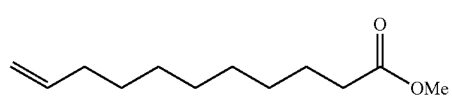 | Methyl undec-10-enoate |
| 18 | 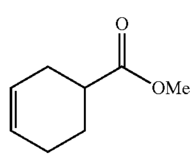 | Methyl cyclohex-3-enecarboxylate |
| 23 | 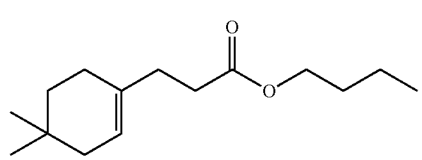 [SMILES: CCCCOC(=O)CCC1=CCC(C)(C)CC1] | Butyl 3-(4,4-dimethylcyclohex-1-en-1-yl)propanoate |

TABLE 4-continued

Structure and names of esters used

| Substrate | Structure | Name |
|---|---|---|
| 24 | (structure of tetramethyldecahydronaphthofuranone) | (3aR,5aS,9aS,9bR)-3a,6,6,9a-Tetramethyldecahydronaphtho[2,1-b]furan-2(3aH)-one |

TABLE 5

Hydrogenation of esters using complex Fe(L-1)(CO)Br$_2$

| Test | Sub. | C/B | Conv. | ROH | Sel. | Isolated yield |
|---|---|---|---|---|---|---|
| 1 | 10[1] | 1000/50000 | 96.5 | 94 | — | — |
| 2 | 10 | 2000/50000 | >99 | >99 | — | 89 |
| 3 | 10[1] | 5000/50000 | >99 | >99 | — | — |
| 4 | 10[2] | 2000/50000 | >99 | >99 | — | — |
| 5 | 11 | 2000/50000 | >99 | 99 | — | 87 |
| 6 | 12 | 2000/50000 | 85 | 85 | — | — |
| 7 | 17 | 2000/50000 | 75 | 70 | >99:1 | 66 |
| 8 | 18 | 2000/50000 | 87 | 86 | >99:1 | — |
| 9 | 23[1] | 5000/50000 | >99 | 92 | >99:1 | — |
| 10 | 24[1] | 2000/50000 | >99 | >99 | — | 98 |

C/B: catalyst/base ratio in ppm relative to the substrate.
Conv.: Conversion (in %, analysed by GC) of esters to the corresponding alcohol after 16 hour. Reaction conditions: H$_2$ gas (50 bar), 100° C., THF (1.7M).
ROH: amount of alcohol in percent in the reaction mixture as analysed by GC
Sel.: Selectivity given as ratio between unsaturated and saturated alcohol as analysed by GC.
[1]Test performed with the preformed and isolated Fe(L-1)(CO)(H)(Br) complex.
[2]Test performed with the preformed and isolated Fe(L-1)(CO)(H)(Cl) complex.

Example 6

Comparative Catalytic Hydrogenation of Methyl Dec-9-Enoate Using Complexes Fe(L-1)(CO)(H)(Br) and Fe(L-1)(CO)(H)(BH$_4$)

A typical experimental procedure is as follows:

A Keim autoclave was charged successfully with a solution of methyl dec-9-enoate (1.84 g, 10 mmol; GC purity of 93.4% containing also 1.4% of methyl decanoate and 2% of methyl dec-8-enoate) in THF (6 ml), followed by the desired complex (0.05 mmol, 0.5 mol %) and the desired amount of base (0.5 to 1.0 mmol, 5 to 10 mol %). The autoclave was then purged with hydrogen gas and pressurised with hydrogen gas at 50 bars and placed in a heating block set at 100° C. After 16 hour, the autoclave was removed and cooled to RT. The reaction mixture was diluted with MTBE (5 ml) and washed with a solution of sat. aq. NH$_4$Cl (5 ml). The organic layer was dried over anh. MgSO$_4$ and filtered. The solvent was removed in vacuo to give an oil which was analysed by GC (DB-Wax).

Under these conditions, several conditions as reported in Table 6 were tested.

TABLE 6

Hydrogenation of methyl dec-9-enoate using complex Fe(L-1)(CO)(H)(Br) and Fe(L-1)(CO)(H)(BH$_4$)

| Test | Base | C/B | Conv. | ROH-9-ene | ROH-8-ene | ROH-sat. |
|---|---|---|---|---|---|---|
| 1 | NaOMe[1] | 2000/50000 | 95 | 88 | 3 | 3 |
| 2 | NaOMe[1] | 5000/50000 | 98 | 91 | 2 | 3 |
| 3 | NaOMe[1,2] | 5000/50000 | 56 | 51 | 2 | 2 |
| 4 | Et$_3$N[3] | 5000/100000 | >99 | 94 | 2 | 3 |
| 5 | NaOMe[3] | 5000/50000 | >99 | 90 | 2 | 6 |

C/B: catalyst/base ratio in ppm relative to the substrate.
Conv.: Conversion (in %, analysed by GC) of esters to the corresponding alcohol after 16 hour. Reaction conditions: H$_2$ gas (50 bar), 100° C., THF (1.7M).
ROH-9-ene: amount of desired alcohol (double bond in position 9) in percent in the reaction mixture as analysed by GC.
ROH-8-ene: amount of alcohol with double bond in position 8 in percent in the reaction mixture as analysed by GC.
ROH-sat: amount of decanol in percent in the reaction mixture as analysed by GC.
[1]Test performed with Fe(L-1)(CO)(H)(Br).
[2]Test performed with addition of styrene (250000 ppm relative to the substrate) according to WO 2013/171302 A1.
[3]Test performed with Fe(L-1)(CO)(H)(BH$_4$).

Example 7

Comparative Catalytic Hydrogenation of Benzaldehyde Using Complexes Fe(L-1)(CO)Br$_2$ and Fe(L-6)(CO)Br$_2$ A typical experimental procedure is as follows:

In a Keim autoclave, charged with a solution of benzaldehyde (1.065 g, 10 mmol) in EtOH (5 ml) was added with a syringe a solution of Fe(L-1/L-6)(CO)HBr (0.5 ml, 0.02 M in THF, 0.01 mmol, 0.1 mol %), prepared by adding at −20° C. a solution of NaEt$_3$BH (0.025 ml at 1M, 0.025 mmol) to a solution of Fe(L-1/L-6)(CO)Br$_2$ (11 mg, 0.02 mmol) in THF (1 ml), followed by solid KOtBu (0.011 g, 0.1 mmol, 1 mol %). The autoclave was pressurised with hydrogen gas at 20 bar and the solution was stirred at RT. After 6 hours, the autoclave was depressurized and an aliquot of the reaction mixture was taken and analysed by GC.

Under these conditions, the hydrogenation of benzaldehyde was compared with complexes Fe(L-1)(CO)Br$_2$ and Fe(L-6)(CO)Br$_2$. The results are reported in Table 7.

TABLE 7

Comparative hydrogenation with Fe(L-1)(CO)Br$_2$/Fe(L-6)(CO)Br$_2$

| Test | Sub. | Iron cpx. | C/B | Conv. | ROH |
|---|---|---|---|---|---|
| Invention | 1 | Fe(L-1)(CO)Br$_2$ | 1000/10000 | 83 | 77 |
| Prior art | 1 | Fe(L-6)(CO)Br$_2$ | 1000/10000 | 14 | 14 |

L-6: see table of example 7.
C/B: catalyst/base ratio in ppm relative to the substrate.
Conv.: Conversion (in %, analysed by GC) of benzaldehyde to the corresponding alcohol after 6 hours.
Reaction conditions: H$_2$ gas (20 bar), RT, EtOH (2M).
ROH: amount of alcohol in percent in the reaction mixture as analysed by GC

Example 8

Catalytic Hydrogenation of Acetophenone with Different Iron Complexes, Ligands L-2 to L-5

A typical experimental procedure is as follows:

In a glove box under argon, a 10 ml scintillation vial equipped with a stirring bar was charged successively with $FeBr_2$ (5.5 mg, 0.025 mmol, 0.5 mol %), bis[2-(dicyclohexylphosphino)ethyl]amine (12.6 mg, 0.027 mmol, 0.54 mol %) and THF (1 ml). The vial was capped with a Teflon lid and the solution was stirred at RT for 15 min resulting in a white suspension. A needle was set through the lid and the vial was placed in an autoclave and pressurized under CO (5 bar) for 1 hour. Then under argon in a glove box, the vial was removed from the autoclave, a deep blue solution had formed, to then was added a solution of $NaBHEt_3$ (40 µl at 1 M, 0.04 mmol, 0.8 mol %) in THF. After stirring at RT for 15 min, a yellow brown solution had formed. Then a solution of acetophenone (2 ml at 2.5 M, 5 mmol) in EtOH and a solution of KOtBu (1 ml at 0.05 M, 0.05 mmol, 1 mol %) in EtOH were successively added to the vial. The vial was placed again in the autoclave which was pressurised with hydrogen (20 bar) and the solution was stirred at RT for 14 hours. The autoclave was depressurised and an aliquot of the reaction mixture was taken and analysed by GC (DB-Wax).

Under these conditions, several ligands (L1-L9) as reported in Table 8, were tested. The results are reported in Table 9.

TABLE 8

Structure of ligands tested

| Structure | Name |
|---|---|
| 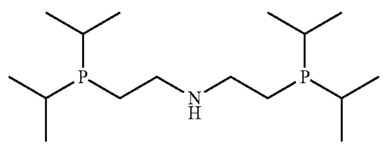 [SMILES: CC(C)P(CCNCCP(C(C)C)C(C)C)C(C)C] | L-1 |
| 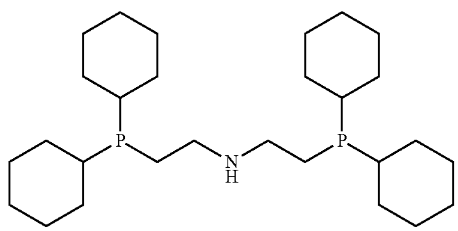 [SMILES: C1CCC(P(CCNCCP(C2CCCCC2)C2CCCCC2)C2CCCCC2)CC1] | L-2 |
| 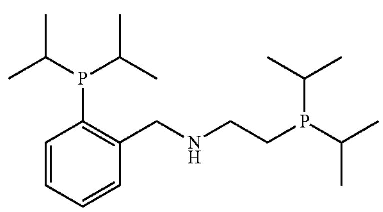 [SMILES: CC(C)P(CCNCc1ccccc1P(C(C)C)C(C)C)C(C)C] | L-4 |
| 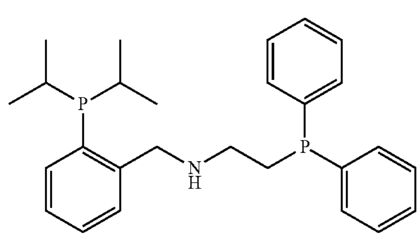 [SMILES: CC(C)P(c1ccccc1CNCCP(c1ccccc1)c1ccccc1)C(C)C] | L-5 |
| 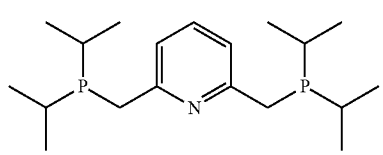 [SMILES: CC(C)P(Cc1cccc(CP(C(C)C)C(C)C)n1)C(C)C] | L-6 (not part of the invention) |

TABLE 8-continued

Structure of ligands tested

| Structure | Name |
|---|---|
| (structure) | L-7 |
| (structure) | L-8 |
| (structure) | L-9 |

Ligands L-1 or L-2 were purchased from *Strem Chemicals* or can be prepared according to Edwards, P. G. *Polyhedron* 1990, 9, 2413-2418.
Ligand L-4 and L-5 were prepared as described below.
Ligand L-6 was prepared according to Milstein *Angew. Chem. Int. Ed*, 2011, 50, 2120.
Ligand L-8 and L-9 were prepared according to Morris, R. H. *J. Am. Chem. Soc.* 2014, 136, 1367-1380.

TABLE 9

Hydrogenation of acetophenone with complex Fe(L-2 to L-5)(CO)HBr

| Test | Ligand | C/B | Conv. | ROH |
|---|---|---|---|---|
| 1 | L-1 | 1000/2000 | >99 | >99 |
| 2 | L-2 | 5000/10000 | 83 | 83 |
| 4 | L-4 | 5000/10000 | >99 | >99 |
| 5 | L-5 | 5000/10000 | >99 | >99 |
| 6 | L-6 | 2000/4000 | >99 | >99 |
| 7 | L-7[1] | 2000/10000 | >99 | >99 |
| 8 | L-8[1] | 2000/10000 | >99 | >99 |
| 9 | L-9[1] | 2000/10000 | >99 | >99 |

C/B: catalyst/base ratio in ppm relative to the substrate.
Conv.: Conversion (in %, analysed by GC) of acetophenone to the corresponding 1-phenylethanol after 14 hours.
Reaction conditions: $H_2$ gas (20 bar), RT, EtOH (1.25M).
ROH: amount of alcohol in percent in the reaction mixture as analysed by GC.
[1]Test performed at $H_2$ gas (25 bar), 50° C., EtOH (M) for 16 h.

Example 9

Synthesis of 2-(diisopropylphosphino)-N-(2-(diisopropylphosphino)benzyl)ethanamine (L-4)

Under argon, to a solution of 2-bromo-benzaldehyde (408.5 mg, 2.2 mmol) in THF (5 ml) was added a solution of 2-(diisopropylphosphino)ethanamine (367.7 mg, 2.2 mmol) in THF (2 ml). More THF (3×1 ml) was added to rinse and the resulting solution was stirred at RT for 15 hours. Then the solvent was removed under vacuum, replaced by some toluene (2 ml) and the solvent removed again under vacuum. The resulting oil was dissolved in THF (20 ml), and cooled by a dry ice/acetone bath at −80° C. Then a solution of tert-BuLi (1.8 ml at 1.35 M in pentane, 2.4 mmol) was added dropwise. After 1 hour at −80° C., $iPr_2PCl$ (370 μl, 2.3 mmol) was added to the yellow-orange solution. The temperature was let warm to 0° C. in 6 hours and then the solution was stirred at RT for another 14 hours. Then, the solvent was removed under vacuum and the resulting yellow white oil was dissolved in MeOH (20 ml). $NaBH_4$ (185.9 mg, 4.9 mmol) was next added in one portion followed by more MeOH (5 ml) and the mixture stirred at RT. After 3 hours, the solvent was eliminated and the residue was dissolved in water (20 ml) and extracted with $Et_2O$ (5×10 ml). The combined organic phases were dried over anh. $K_2CO_3$. After filtration, the solvent was removed under vacuum to give a yellow oil which was purified on a Alox column (neutral type 507C) eluted with pentane/$Et_2O$ (1/1) and then $Et_2O$ to give the desired product L-4 (449.2 mg, 1.2 mmol, 55%) as a colorless oil.

$^1$H-NMR ($C_6D_6$): 0.91 (dd, J=6.9, 11.8 Hz, 6H), 0.98 (dd, J=6.9, 13.8 Hz, 6H), 1.01 (dd, J=7.0, 16.7 Hz, 6H), 1.09 (dd, J=6.9, 14.7 Hz, 6H), 1.5-1.62 (m, 4H), 1.65 (brs, NH), 1.96 (dsept, J=2.4, 6.9 Hz, 2H), 2.89 (q, J=7.7 Hz, 2H), 4.26 (d, J=2.1 Hz, 2H), 7.09 (dt, J=1.4, 7.4 Hz, 1H), 7.17 (dt, J=1.3, 7.4 Hz, 1H), 7.3-7.34 (m, 1H), 7.52 (ddd, J=1.1, 3.9, 5.6 Hz, 1H).

$^{13}$C-NMR ($C_6D_6$): 18.92 (d, JCP=10.2 Hz, CH3), 19.78 (d, JCP=10.8 Hz, CH3), 20.26 (d, JCP=16.6 Hz, CH3), 20.52 (d, JCP=19.4 Hz, CH3), 23.51 (d, JCP=19.4 Hz, CH2), 23.7 (d, JCP=13.7 Hz, CH), 24.62 (d, JCP=13.5 Hz, CH), 48.71 (d, JCP=24.2 Hz, CH2), 52.99 (d, JCP=23.6 Hz, CH2), 126.52 (s, CH arom), 128.89 (s, CH arom), 129.79 (d, JCP=5.9 Hz, CH arom), 132.59 (d, JCP=3.2 Hz, CH arom), 135.1 (d, JCP=20.9 Hz, C arom), 148.16 (d, JCP=24.5 Hz, C arom).

$^{31}P\{^1H\}$-NMR ($C_6D_6$): −7.37 (s), −1.59 (s).

Example 10

Synthesis of N-(2-(diisopropylphosphino)benzyl)-2-(diphenylphosphino)ethanamine (L-5)

Under argon, to a solution of (E)-N-(2-bromobenzylidene)-2-(diphenylphosphino) ethanamine (1.0026 g, 2.53 mmol) in THF (50 ml) cooled by a dry ice/acetone bath at −80° C. was added a solution of tert-BuLi (1.4 ml at 1.88 M in pentane, 2.63 mmol) dropwise. After 1 hour at −80° C., iPr$_2$PCl (420 μl, 2.64 mmol) was added to the orange solution. The temperature was let warm to room temperature over-night (16 hours). Then, the solvent was removed from the yellow solution under vacuum and the resulting orange oil was dissolved in MeOH (20 ml). NaBH$_4$ (241.7 mg, 5.7 mmol) was next added in one portion followed by more MeOH (5 ml) and the mixture stirred at RT. After 3 hours, the solvent was eliminated and the residue was dissolved in water (20 ml) and extracted with Et$_2$O (5×10 ml). The combined organic phases were dried over anh. K$_2$CO$_3$. After filtration, the solvent was removed under vacuum to give a white-yellow oil which was purified on an Alox column (neutral type 507C) eluted with pentane/Et$_2$O (2/1) and then Et$_2$O to give the desired product L-5 (662.2 mg, 1.5 mmol, 59%) as a colorless oil.

$^1$H-NMR ($C_6D_6$): 0.87 (dd, J=6.9, 11.8 Hz, 6H), 2.13 (dd, J=6.9, 14.8 Hz, 6H), 1.55 (brs, NH), 1.93 (dsept, J=2.4, 6.9 Hz, 2H), 2.26 (app t, J=7.5 Hz, 2H), (app q, J=8.6 Hz, 2H), 4.16 (d, J=2.1 Hz, 2H), 7.02-7.12 (m, 6H), 7.14-7.18 (m, 2H), 7.28-7.32 (m, 1H), 7.38-7.41 (m, 1H), 7.41-7.47 (m, 4H).

$^{13}$C-NMR ($C_6D_6$): 19.71 (d, JCP=10.7 Hz, CH3), 20.49 (d, JCP=19.6 Hz, CH3), 24.57 (d, JCP=13.2 Hz, CH), 29.98 (d, JCP=13.1 Hz, CH2), 46.44 (d, JCP=20.6 Hz, CH2), 52.69 (d, JCP=23.5 Hz, CH2), 126.51 (s, CH arom), 128.57 (d, JCP=6.9 Hz, CH arom), 128.64 (d, JCP=6.5 Hz, CH arom), 128.89 (s, CH arom), 129.80 (d, JCP=5.7 Hz, CH arom), 132.56 (d, JCP=2.9 Hz, CH arom), 133.16 (d, JCP=18.7 Hz, CH arom), 135.00 (d, JCP=20.9 Hz, C arom), 139.79 (d, JCP=14.4 Hz, C arom), 147.94 (d, JCP=24.2 Hz, C arom)

$^{31}P\{^1H\}$-NMR (162 MHz, $C_6D_6$): −7.44 (s), −19.77 (s).

What is claimed is:

1. A process for the reduction by hydrogenation, using molecular $H_2$, of a $C_3$-$C_{70}$ substrate containing one or two carbonyl or carboxylic functional group into the corresponding alcohol, or diol, characterized in that said process is carried out in the presence of a base and at least one catalyst or pre-catalyst in the form of an iron complex of formula

[Fe(L3)(L')Y$_a$](Z)$_b$     (1)

wherein L3 is a compound of formula:

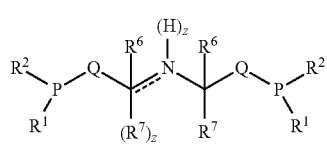

(A)

wherein in (A):
the dotted line indicates a single or double bond;
z is 0 or 1 when the carbon-nitrogen bond with the dotted line represents a double or single bond respectively;
R$^1$ and R$^2$, when taken separately, represent, simultaneously or independently, a linear, branched or cyclic C$_1$ to C$_{10}$ alkyl or alkenyl group optionally substituted, a C$_6$ to C$_{10}$ aromatic group optionally substituted; said groups R$^1$ and R$^2$, when taken together, may form a saturated or unsaturated ring optionally substituted, having 5 to 10 atoms and including the phosphorus atom to which said R$^1$ and R$^2$ groups are bonded;
R$^6$ and R$^7$ represent, simultaneously or independently, a hydrogen atom, a linear, branched or cyclic C$_1$ to C$_6$ alkyl or alkenyl group optionally substituted, a C$_6$-C$_{10}$ aromatic group optionally substituted; when the dotted line represent a single bond, two R$^6$ taken together, may form a saturated heterocycle, optionally substituted and optionally containing one or two additional nitrogen or oxygen atoms, containing 5 to 10 atoms and including the N atom and the carbon atoms to which said R$^6$ groups are bonded respectively; and
Q represents:
a group of formula

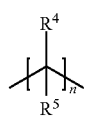

(i)

wherein n is an integer from 1 to 3, and
R$^4$ and R$^5$ represent, simultaneously or independently, a hydrogen atom, a linear, branched or cyclic C$_1$ to C$_6$ alkyl or alkenyl group optionally substituted, a C$_6$-C$_{10}$ aromatic group optionally substituted; two distinct R$^4$ and/or R$^5$ groups, taken together, may form a C$_5$ to C$_8$, saturated ring optionally substituted, including the carbon atoms to which each of said R$^4$ or R$^5$ group is bonded; or
a diphenyl, dinaphthyl, C$_5$-C$_{12}$ metallocediyl, phenylene or naphthylene group optionally substituted; and
the optional substituents of R$^4$, R$^5$, R$^6$ and R$^7$ are one or two halogen, C$_1$ to C$_{10}$ alkoxy groups, halo- or perhalo-hydrocarbon, COOR, NR$_2$, quaternary amine or R groups, wherein R is a C$_1$ to C$_6$ alkyl, or a C$_5$ to C$_{12}$ cycloalkyl, aralkyl or aromatic group being also optionally substituted by one, two or three halogen, sulfonates groups or C$_1$-C$_8$ alkyl, alkoxy, amino, nitro, sulfonates, halo- or perhalo-hydrocarbon or ester groups; and
the optional substituents of R$^1$, R$^2$ and Q, when said groups are or contain phenyl or aromatic groups, are one to three C$_1$ to C$_5$ alkoxy groups, C$_1$ to C$_4$ alkyl groups, or NR groups, wherein R is a C$_1$ to C$_6$ alkyl C$_5$ to C$_6$ cycloalkyl;
L' represents a CO or C$_{1-11}$ isonitrile compound;
each Y represents, simultaneously or independently, a hydrogen or halogen atom, a hydroxyl group, or a C$_1$-C$_6$ alkoxy or carboxylic radical or a BH$_4$ or AlH$_4$ group;
Z represents a halogen atom, a hydroxyl group, or a C$_1$-C$_6$ alkoxy or carboxylic radical or a BH$_4$ or AlH$_4$ group; and
(a+b)=2 with a being 1 or 2.

2. A process according to claim 1, wherein said ligand L3 is a compound of formula

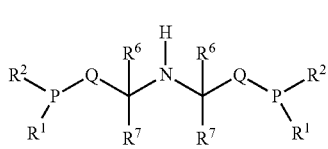
(B)

wherein the $R^1$, $R^2$, $R^6$ and $R^7$ have the same meaning as recited in claim 1.

3. A process according to claim 1, wherein said substrate is a $C_5$-$C_{30}$ compound of formula

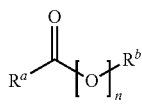
(I)

wherein n represents 0 or 1;
$R^a$ and $R^b$, taken together, represent a $C_3$-$C_{20}$ hydrocarbon group, optionally substituted and optionally comprising one, two or three oxygen or nitrogen atoms; or, when said
$R^a$ and $R^b$ are taken separately,
$R^a$ represents a hydrogen atom or $R^b$ group;
$R^b$ represents a $C_1$-$C_{30}$ hydrocarbon group, optionally substituted and optionally comprising one, two or three oxygen or nitrogen atoms; and
the optional substituents of $R^a$ and $R^b$ are one, two or three halogen, $COOR^c$, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

4. A process according to claim 3, wherein said substrate is a compound of formula (I) wherein $R^a$ represent a hydrogen atom or $R^b$ group, and $R^b$ group represents a linear, branched or cyclic $C_3$-$C_{18}$ aromatic, alkyl, alkenyl or alkanedienyl group optionally substituted; or $R^a$ and $R^b$ are bonded together and form a $C_5$-$C_{20}$ saturated or unsaturated linear, branched, mono-, di- or tri-cyclic group, optionally substituted.

5. A process according to claim 3, wherein said substrate is a compound of formula (I) as defined in claim 3, wherein
when n is 1 and $R^a$ is an alkenyl or alkadienyl group, that said group is not an alk-1-enyl or an alka-1,3-dienyl group; or
when n is 0 and $R^a$ is an alkenyl or alkadienyl group, that said group is an alk-1-enyl or an alka-1,3-dienyl group; or
when n is 0 and $R^a$ is a hydrogen atom, $R^b$ represent a branched or cyclic hydrocarbon group wherein the branching is in the alpha position relative to the CHO group of the substrate.

6. A process according to claim 3, wherein in said substrate n is 1.

7. A process according to claim 3, wherein $R^a$ and $R^b$, taken together, represent a $C_4$-$C_{20}$, hydrocarbon group, optionally substituted and optionally comprising one, two or three oxygen or nitrogen atoms.

8. A process according to claim 3, wherein $R^c$ is a $C_1$ to $C_4$ linear or branched alkyl or alkenyl group.

9. A process according to claim 1, wherein said base has a $pK_a$ above 10.

10. A process according to claim 1, wherein said base is a alkaline or alkaline-earth metal carbonates, an alkaline or alkaline-earth metal hydroxides, $C_{1-10}$ amidures, $C_{10-26}$ phosphazene or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

11. A process according to claim 1, wherein said substrate is a $C_5$-$C_{30}$ compound of formula

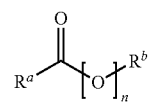
(I)

wherein n represents 0 or 1;
$R^a$ and $R^b$, taken together, represent a $C_3$-$C_{20}$ hydrocarbon group, optionally substituted and optionally comprising one, two or three oxygen or nitrogen atoms; or, when said
$R^a$ and $R^b$ are taken separately,
$R^a$ represents a hydrogen atom or $R^b$ group;
$R^b$ represents a $C_1$-$C_{30}$ hydrocarbon group, optionally substituted and optionally comprising one, two or three oxygen or nitrogen atoms; and
the optional substituents of $R^a$ and $R^b$ are one, two or three halogen, $COOR^c$, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

12. A process according to claim 11, wherein $R^a$ and $R^b$, taken together, represent a $C_4$-$C_{20}$, hydrocarbon group, optionally substituted and optionally comprising one, two or three oxygen or nitrogen atoms.

13. A process according to claim 11, wherein $R^c$ is a $C_1$ to $C_4$ linear or branched alkyl or alkenyl group.

14. A process according to claim 1, wherein said complex is of formula $$[Fe(L3)(L')Y_2] \qquad (2)$$

wherein L3 L' and Y have the same meaning as in claim 1.

15. A process according to claim 14, wherein said ligand L3 is a compound of formula

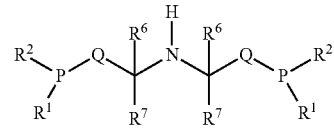
(B)

wherein the $R^1$, $R^2$, $R^6$ and $R^7$ have the same meaning as recited in claim 1.

16. A process according to claim 14, wherein said substrate is a $C_5$-$C_{30}$ compound of formula

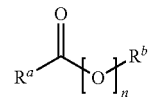
(I)

wherein n represents 0 or 1;
$R^a$ and $R^b$, taken together, represent a $C_3$-$C_{20}$ hydrocarbon group, optionally substituted and optionally comprising one, two or three oxygen or nitrogen atoms; or, when said $R^a$ and $R^b$ are taken separately, $R^a$ represents a hydrogen atom or $R^b$ group;

$R^b$ represents a $C_1$-$C_{30}$ hydrocarbon group, optionally substituted and optionally comprising one, two or three oxygen or nitrogen atoms; and the optional substituents of $R^a$ and $R^b$ are one, two or three halogen, $COOR^c$, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

17. A process according to claim 16, wherein in said substrate n is 1.

18. A process according to claim 16, wherein $R^a$ and $R^b$, taken together, represent a $C_4$-$C_{20}$, hydrocarbon group, optionally substituted and optionally comprising one, two or three oxygen or nitrogen atoms.

19. A process according to claim 16, wherein $R^c$ is a $C_1$ to $C_4$ linear or branched alkyl or alkenyl group.

20. The process of claim 14, wherein said complex is (Fe(L1)(CO) Br2) and (Fe(L1)(CO)HBr), wherein L1 is bis[2-(di-isopropylphosphino)ethyl] amine.

21. A process according to claim 1 wherein the iron complex has the formula $$[Fe(L3)(L')Y_2] \quad (2)$$

wherein L' represents a CO or $C_1$-$_{11}$ isonitrile compound; each Y represents, simultaneously or independently, a hydrogen or halogen atom, a hydroxyl group, or a $C_1$-$C_6$ alkoxy or carboxylic radical or a $BH_4$ or $AlH_4$ group; L3 is a tridentate ligand of formula

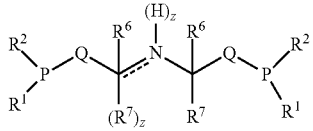

(A)

wherein the dotted line indicates a single or double bond; z is 0 or 1 when the carbon-nitrogen bond with the dotted line represents a double or single bond respectively;

$R^1$ and $R^2$, when taken separately, represent, simultaneously or independently, a linear, branched or cyclic $C_1$ to $C_{10}$ alkyl or alkenyl group optionally substituted, a $C_6$ to $C_{10}$ aromatic group optionally substituted; said groups $R^1$ and $R^2$, when taken together, may form a saturated or unsaturated ring optionally substituted, having 5 to 10 atoms and including the phosphorus atom to which said $R^1$ and $R^2$ groups are bonded;

$R^6$ and $R^7$ represent, simultaneously or independently, a hydrogen atom, a linear, branched or cyclic $C_1$ to $C_6$ alkyl or alkenyl group optionally substituted, a $C_6$-$C_{10}$ aromatic group optionally substituted; when the dotted line represent a single bond, two $R^6$ taken together, may form a saturated heterocycle, optionally substituted and optionally containing one or two additional nitrogen or oxygen atoms, containing 5 to 10 atoms and including the N atom and the carbon atoms to which said $R^6$ groups are bonded respectively; and Q represents:

a group of formula

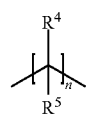

(i)

wherein n is an integer from 1 to 3, and $R^4$ and $R^5$ represent, simultaneously or independently, a hydrogen atom, a linear, branched or cyclic $C_1$ to $C_6$ alkyl or alkenyl group optionally substituted, a $C_6$-$C_{10}$ aromatic group optionally substituted; two distinct $R^4$ and/or $R^5$ groups, taken together, may form a $C_5$ to $C_8$, saturated ring optionally substituted, including the carbon atoms to which each of said $R^4$ or $R^5$ group is bonded; or a diphenyl, dinaphthyl, $C_5$-$C_{12}$ metallocediyl, phenylene or naphthylene group optionally substituted; and the optional substituents of $R^4$, $R^5$, $R^6$ and $R^7$ are one or two halogen, $C_1$ to $C_{10}$ alkoxy groups, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups; and the optional substituents of $R^1$ and $R^3$ and Q, in particular when said groups are or contains phenyl or aromatic groups or moieties, one to three $C_1$ to $C_5$ alkoxy groups, $C_1$ to $C_4$ alkyl groups, or NR groups, wherein R is a $C_1$ to $C_6$ alkyl $C_5$ to $C_6$ cycloalkyl.

22. A process according to claim 21, wherein L3 is a compound of formula

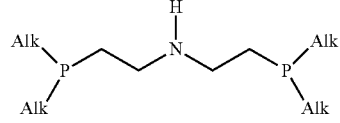

(C)

wherein Alk is a $C_3$-$_{10}$, or even $C_3$-$_6$, branched or cyclic alkyl group.

* * * * *

UNITED STATES PATENT AND TRADEMARK OFFICE
CERTIFICATE OF CORRECTION

PATENT NO. : 10,053,475 B2
APPLICATION NO. : 15/105927
DATED : August 21, 2018
INVENTOR(S) : Quintaine et al.

It is certified that error appears in the above-identified patent and that said Letters Patent is hereby corrected as shown below:

In the Claims

Column 24:
Line 63, Claim 1 after "Z represents a", insert -- moiety attached to or part of $R^7$ or H, respectively, wherein the moiety is a --.

Signed and Sealed this
Ninth Day of October, 2018

Andrei Iancu
*Director of the United States Patent and Trademark Office*